United States Patent
Kwok et al.

(10) Patent No.: US 6,633,358 B1
(45) Date of Patent: Oct. 14, 2003

(54) METHODS AND APPARATUS FOR MEASUREMENT OF LC CELL PARAMETERS

(75) Inventors: Hoi-Sing Kwok, Kowloon (HK); Shu-Tuen Tang, New Territories (HK)

(73) Assignee: The Hong Kong University of Science and Technology, Hong Kong (HK)

( * ) Notice: Subject to any disclaimer, the term of this patent is extended or adjusted under 35 U.S.C. 154(b) by 294 days.

(21) Appl. No.: 09/712,228

(22) Filed: Nov. 15, 2000

(51) Int. Cl.$^7$ ............................................... G02F 1/13
(52) U.S. Cl. ........................................................ 349/136
(58) Field of Search ........................ 356/364; 349/136, 349/180

(56) References Cited

U.S. PATENT DOCUMENTS

| | | | | |
|---|---|---|---|---|
| 5,311,284 A | * | 5/1994 | Nishino | 356/364 |
| 5,504,581 A | * | 4/1996 | Nagata et al. | 356/364 |
| 5,532,823 A | * | 7/1996 | Fukui et al. | 356/364 |
| 5,627,645 A | * | 5/1997 | Imagawa et al. | 356/364 |
| 5,903,352 A | * | 5/1999 | Ohsaki et al. | 356/364 |
| 6,088,115 A | * | 7/2000 | Ohsaki et al. | 356/445 |
| 6,317,208 B1 | * | 11/2001 | Hirosawa | 356/364 |
| 6,348,966 B1 | * | 2/2002 | Hirosawa | 356/364 |
| 6,473,180 B2 | * | 10/2002 | Hirosawa | 356/364 |

OTHER PUBLICATIONS

Tang, S.T. et al, "A new method to measure the twist angle and cell gap of liquid–crystal cells", SID '98 Digest, pps. 552–555.

Shao, X. et al, "A new method to measure thickness of twist nematic liquid crystal cells", Euro Display '96, pps. 309–312.

Lien, A., "Simultaneous measurement of twist angle and cell gap of a twisted nematic cell by an optical method"; IEEE 1991, pps. 192–194.

Sumiyoshi, K. et al, "Two new measurement methods for determining TN structure"; Liquid Crystals, 1997, vol. 22, No. 3, pps. 327–333.

Raynes, E.P., "The optical properties of supertwisted liquid crystal layers", Molecular Crystals and Liquid Crystal Letters vol. 4(3–4), pps. 69–75, 1987.

Tang, S.T. et al, "Application of 2x2 and 4x4 matrices to the modelling of all nematic liquid crystal displays", SPIE vol. 3800, pps. 87–92, Jul. 1999.

\* cited by examiner

*Primary Examiner*—James Dudek
(74) *Attorney, Agent, or Firm*—Burns, Doane, Swecker & Mathis, L.L.P.

(57) ABSTRACT

Three measuring methods and apparatus for determining the twist angle ($\phi$) and retardation value (d$\Delta$n) of any twisted nematic liquid crystal (LC) cell are disclosed. These methods make use of a monochromatic light source such as a laser beam. Twist angle and retardation values an be obtained by data fitting using data obtained by adjusting only the polarizes and the LC cell orientation. No retardation wave-plate is needed.

19 Claims, 5 Drawing Sheets

1. Monochromatic Light Source
8. Photodetector
7. Polarizing Beam Splitter
5. LC cell
9. Partial Mirror
3. Analyzer
4. Photodetector

METHODS AND APPARATUS FOR MEASUREMENT OF LC CELL PARAMETERS

The present invention relates to novel methods of measuring the parameters of twisted nematic liquid crystal devices including the twist angle, twist sense and retardation value (defined as the product of the cell gap and the liquid crystal birefringence). Apparatus for performing these measurements are also disclosed.

BACKGROUND OF THE INVENTION AND PRIOR ART

Conventional liquid crystal displays, including twisted nematic (TN) and super-twisted nematic (STN) LCDs, have several important design parameters, including the twist angle $\phi$ of the liquid crystal alignment and the retardation value which is defused as a product of the cell gap d and the birefringence $\Delta n$ of the liquid crystal material (d$\Delta$n). These two parameters are important in determining the optical performance of the liquid crystal display. Thus the ability to determine these two parameters is important both for product development and for quality assurance.

There have been several measurement methods proposed and there exists also commercially available equipment. The measurement methods can be divided into two categories, those that require spectral measurements and those employing monochromatic light sources. All that methods use the Jones matrix as the mathematical tool. Commercially available equipment generally use the spectral method. Such machines can measure twist angle, twist sense and retardation of the LCD without any prior knowledge of the LCD rubbing directions. Monochromatic light source methods reported previously are more limited and can only measure cell gap of liquid crystal cells with known twist angles. A wave-plate compensation method can also be used to measure both the twist angle and the cell gap of an unknown LCD. Also proposed is a method for determining TN structure without using the wave-plane, this uses a rotating analyzer method. However the twist sense cannot be determined.

The present invention provides methods that can give the twist angle retardation and twist sense of any unknown LCD without using any wave-plate and without any a priori knowledge of the LCD rubbing conditions. It uses a monochromatic light source and is therefore easy to implement and economical to setup.

SUMMARY OF THE INVENTION

According to the present invention there is provided method of obtaining the twist angle and retardation value of a liquid crystal cell comprising, locating the liquid crystal cell between a first polarizer and a second polarizer serving as an analyzer, providing an input monochromatic light source and means for measuring the light transmitted through the analyzer, and:

(a) fix the polarizer-analyzer angle $\alpha$, at any fixed angle,
(b) rotate the liquid crystal cell while recording the light transmission
(c) note the maximum ($K_1(\alpha_0)+K_2$) and minimum ($K_1(\alpha_0)$) values of the transmission from step (b), and
(d) solve equation $$K_1(\alpha_0) = \left\{ \cos\beta\cos(\phi - \alpha_0) + \frac{\sin\beta\sin(\phi - \alpha_0)}{\sqrt{1+r^2}} \right\}^2$$

$$K_2 = \frac{r^2}{1+r^2}\sin^2\beta$$

simultaneously to obtain ($\phi$, d$\Delta$n) either graphically or numerically.

According to the present invention throe is further provided a method of obtaining the twist angle and retardation value of a liquid crystal cell comprising, locating the liquid crystal cell between a first polarizer and a second polarizer serving as an analyzer, providing an input monochromatic light source and means for measuring the light transmitted through the analyzer, and;

(a) fixing the polarizers in the characteristic directions of said cell whereby the angle ($\Psi$) between said directions is then determined,
(b) rotate the liquid crystal cell while recording the light transmitted through the analyzer,
(c) obtain the transmission minimum (1–$K_2$) and then solve equations $$K_2 = \frac{r^2}{1+r^2}\sin^2\beta$$

$$\frac{\phi}{\sqrt{\delta^2+\phi^2}}\tan\sqrt{\delta^2+\phi^2} = \tan(\phi - \psi)$$

simultaneously to obtain ($\phi$, d$\Delta$a) graphically or numerically.

According to the present invention there is further provided a method of obtaining the twist angle and retardation value of a liquid crystal cell comprising locating said liquid crystal cell between a horizontal polarizer and a Stokesmeter and providing an input source of monochromatic light, and (a) rotating the liquid crystal cell while recording the Stokes parameters, and
(b) obtaining the $S_1$ maximum and minimum and then solve equations $$K_1(\alpha_0) = \left\{ \cos\beta\cos(\phi - \alpha_0) + \frac{\sin\beta\sin(\phi - \alpha_0)}{\sqrt{1+r^2}} \right\}^2$$

$$K_2 = \frac{r^2}{1+r^2}\sin^2\beta$$

to obtain ($\phi$, d$\Delta$n) through the equation $$I_{11} = \frac{1+S_1}{2}, \quad \text{or}$$

(c) obtain the $S_2$ maximum and minimum and then solve equations $$K_2 = \frac{r^2}{1+r^2}\sin^2\beta$$

$$\frac{\phi}{\sqrt{\delta^2+\phi^2}}\tan\sqrt{\delta^2+\phi^2} = \tan(\phi - \psi)$$

to obtain (φ, dΔn) through the equation $$I_{45} = \frac{1+S_2}{2}, \quad \text{or}$$

(d) obtain the characteristic angle Ψ and the maximum |S₃| and then solve the equations $$\frac{\phi}{\sqrt{\delta^2+\phi^2}}\tan\sqrt{\delta^2+\phi^2} = \tan(\phi-\psi)$$

$$S_3 = \pm J/\cos(\phi-\psi)$$

simultaneously to obtain (φ, dΔn).

According to the present invention there is further provided a method of obtaining the average tilt angle of a liquid crystal cell by a crystal rotation method comprising locating said liquid crystal cell between a horizontal polarizer and a Stokesmeter and providing an input source of monochromatic light, and (a) rotating the liquid crystal cell while recording the Stokes parameters,
(b) measure the retardation maximum against rotation angle is to calculate the avenge tilt angle.

According to the present invention there is further provided a method of obtaining the characteristic directions of a liquid crystal cell comprising locating the liquid crystal cell between a first polarizer and a second polarizer serving as an analyzer, providing an input monochromatic light source and means for measuring the light transmitted through the analyzer, and:

(a) aligning the analyzer to be in the same direction as the polarizer,
(b) rotating the liquid crystal cell to obtain a transmission maximum wherein the input polarizer bisects the two characteristic directions,
(c) with the polarizer, the bisector and the analyzer aligned in the same orientation rotate the liquid crystal cell and analyzer with a magnitude ratio of 1:2 until maximum transmission is obtained wherein the polarizer and analyzer are in the primary and secondary characterization directions respectively.

According to the present invention there is further provided a method of obtaining the characteristic directions of a liquid crystal cell comprising locating the liquid crystal cell between a polarizing beam splitter and a polarizer serving as an analyzer, providing an input monochromatic light source and a first photodetector for measuring the light transmitted through the analyzer and a second photodetector for detecting light reflected from the liquid crystal cell, and:

(a) rotate the liquid crystal cell until the second photodetector measures zero intensity wherein the input polarization is in the primary characteristic direction;
(c) fix the liquid crystal cell and then rotate the analyzer to obtain a maximum first photodetector reading wherein the analyzer is in the secondary characteristic direction.

According to the present invention there is further provided a method of obtaining the retardation value of a reflective liquid crystal comprising locating the liquid crystal cell between a polarizing beam splitter and a polarizer serving as an analyzer, providing an input monochromatic light source and a first photodetector for measuring the light transmitted through the analyzer and a second photodetector for detecting light reflected from the liquid crystal cell, and:

(a) rotating the reflective liquid crystal cell until the second photodetector measures zero intensity,
(b) obtaining the retardation value can be obtained by solving the equation $$\frac{\phi}{\sqrt{\delta^2+\phi^2}}\tan\sqrt{\delta^2+\phi^2} = \tan 2\alpha^*$$

with the twist angle and rubbing direction known in advance.

According to another aspect of the present invention there is provided apparatus for measuring the twist angle and retardation value of a liquid crystal cell comprising a monochromatic light source, an input polarizer, a rotary stage for the a liquid crystal cell under test, a rotary stage for an output analyzer, a photodetector to detect the transmission intensity, and a computer for controlling the rotary stages, receiving data from the photodetector and being programmed to solving the equations:

$$K_1(\alpha_0) = \left\{\cos\beta\cos(\phi-\alpha_0) + \frac{\sin\beta\sin(\phi-\alpha_0)}{\sqrt{1+r^2}}\right\}^2,$$

$$K_2 = \frac{r^2}{1+r^2}\sin^2\beta, \quad \text{and} \quad \frac{\phi}{\sqrt{\delta^2+\phi^2}}\tan\sqrt{\delta^2+\phi^2} = \tan(\phi-\psi).$$

According to the present invention there is further provided apparatus for measuring the twist angle and retardation value and tilt angle of a liquid crystal cell comprising a monochromatic light same, an input polarizer, a rotary stage for the liquid crystal cell under test, a Stokesmeter to measure the output light Stokes parameters and a computer for controlling the rotary stages, receiving data from the Stokesmeter and for solving the equations:

$$K_1(\alpha_0) = \left\{\cos\beta\cos(\phi-\alpha_0) + \frac{\sin\beta\sin(\phi-\alpha_0)}{\sqrt{1+r^2}}\right\}^2,$$

$$K_2 = \frac{r^2}{1+r^2}\sin^2\beta,$$

$$I_{11} = \frac{1+S_1}{2}, \quad \frac{\phi}{\sqrt{\delta^2+\phi^2}}\tan\sqrt{\delta^2+\phi^2} = \tan(\phi-\psi),$$

$$I_{45} = \frac{1+S_2}{2}, \quad \text{and}$$

$$S_3 = \pm J/\cos(\phi-\psi).$$

According to the present invention there is further provided apparatus for measuring the twist angle and retardation value of a liquid crystal cell comprising a monochromatic light source, an input polarizing beam splitter, a rotary stage for the liquid crystal cell under test, a partial mirror for characteristic angle setting, a rotary stage for the output analyzer, a first photodetector to detect the transmission intensity, a second photodetector to detector the reflected light intensity, and a computer for controlling the rotary stage, receiving data from the photodetectors and for solving the equations:

$$K_1(\alpha_0) = \left\{\cos\beta\cos(\phi-\alpha_0) + \frac{\sin\beta\sin(\phi-\alpha_0)}{\sqrt{1+r^2}}\right\}^2,$$

-continued $$K_2 = \frac{r^2}{1+r^2}\sin^2\beta, \quad \frac{\phi}{\sqrt{\delta^2+\phi^2}}\tan\sqrt{\delta^2+\phi^2} = \tan 2\alpha^*, \quad \text{and}$$

$$\frac{\phi}{\sqrt{\delta^2+\phi^2}}\tan\sqrt{\delta^2+\phi^2} = \tan(\phi-\psi).$$

BRIEF DESCRIPTION OF THE DRAWINGS

Some embodiments of the invention will now be described by way of example and with reference to the accompanying drawings, in which.

DETAILED DESCRIPTION OF THE PREFERRED EMBODIMENTS

The invention here disclosed provides methods and apparatus for measuring the twist angle, retardation and twist sense of a twisted nematic liquid crystal device. A monochromatic light source is used. No wave-plate is needed. A first method employs only a pair of polarizers at fixed angles and a photodetector. By measuring the transmission maximum and minimum, and solving a set of equations, the twist angle and LC cell retardation an be obtained. A second method uses the polarizer pair in a specific configuration and also a transmission minimum is needed to solve for the twist angle and retardation. A third method uses only the input polarizer and replaces the analyzer and detector of previous methods by a Stokesmeter. It measures only the Stokes parameters of the system to determine the twist angle, retardation and twist sense.

To accomplish these measurements, three types of instrument configurations are disclosed. The first type uses polarizer pairs and the photodetector in a straight light path. The second type uses a polarizing beam splitter and a T-shaped tight path to accommodate both transmissive and reflective LC cells measurement. The third type uses a Stokesmeter to replace the analyzer and the light detector for measuring light polarization.

Before a description of preferred embodiments of the invention is given, the principles behind the present invention are presented first.

Figure 1:
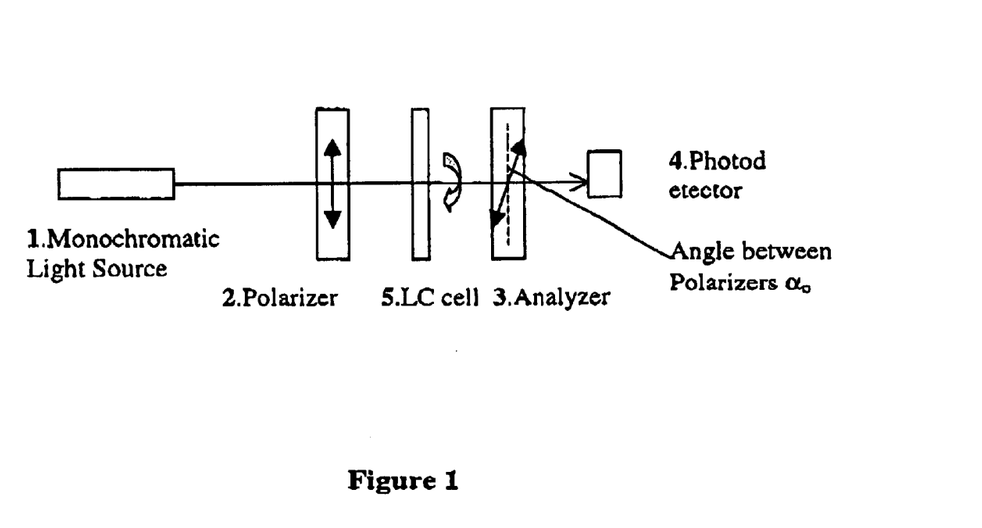
FIG. 1 shows a schematic of a first embodiment of the invention.

A conceptual set-up for polarization analysis of the present inventions is shown in FIG. 1. This consists of a monochromatic light source 1, a pair of polarizers 2 & 3, a photodetector 4 and the liquid crystal cell under test 5 in between the polarizers.

To consider the transmission of light when a twisted nematic liquid crystal cell 5 is placed between the polarizers 2 & 3, a very useful formula derived by Raynes is $$T = \left\{\cos\beta\cos(\phi+\alpha-\gamma) + \frac{\sin\beta}{\sqrt{1+r^2}}\sin(\phi+\alpha-\gamma)\right\}^2 + \quad (1)$$

$$\frac{r^2}{1+r^2}\sin^2\beta\cos^2(\phi-\alpha-\gamma)$$

where α and γ are respectively the input and output polarizer angle related to the LC cell input director, φ is the LC cell twist angle, β and r are defined as $$\beta = \phi\sqrt{1+r^2} \quad \text{and} \quad r = \left(\frac{d\Delta n}{\phi\lambda}\right)\pi$$

with d is the cell gap thickness, Δn is the LC birefrigence and λ is the monochromatic incident light wavelength.

Let the angle between the front polarizes and the rear polarizer be $\alpha_0$ such that $\alpha_0=\gamma-\alpha$. Then equation (1) changes to $$T = \left\{\cos\beta\cos(\phi-\alpha_0) + \frac{\sin\beta}{\sqrt{1+r^2}}\sin(\phi-\alpha_0)\right\}^2 + \quad (2)$$

$$\frac{r^2}{1+r^2}\sin^2\beta\cos^2(\phi-2\alpha-\alpha_0)$$

or in short form $$T(\alpha_0,\alpha) \times K_1(\alpha_0) + K_2\cos^2(\phi-2\alpha-\alpha_0) \quad (3)$$

with $$K_1(\alpha_0) = \left\{\cos\beta\cos(\phi-\alpha_0) + \frac{\sin\beta\sin(\phi-\alpha_0)}{\sqrt{1+r^2}}\right\}^2 \quad \text{and} \quad (4)$$

$$K_2 = \frac{r^2}{1+r^2}\sin^2\beta \quad (5)$$

Figure 6:
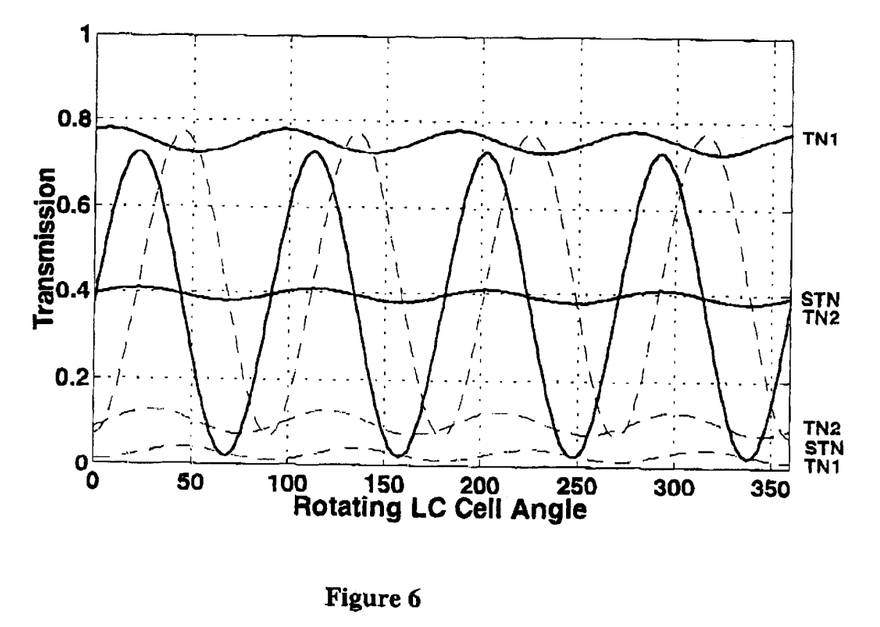
FIG. 6 shows the sinusoidal curves for two TN cells and one STN cells with parameters as these given in FIG. 4, the dotted line represents results of a parallel polarize configuration with $\alpha_0=0$ while the solid line represents results of a 45° analyzer configuration with $\alpha_0=45°$.

If the LC cell is rotated, such that the input polarizes angle α changes gradually, then equation (3) shows that the light transmission is a sinusoidal function with a maximum value of $K_1(\alpha_0)+K_2$ and a minimum value of $K_1(\alpha_0)$. Note that the amplitude of the sinusoidal curve, which is defined as the value of the maxima minus the minima, is a characteristic of the particular LC cell. It does not change with the polarizer-analyzer angle $\alpha_0$ and it is always equals to $K_2$. On the other hand, the minimum value $K_1(\alpha_0)$ of the sinusoidal curve is a function of the polarizer-analyzer angle $\alpha_0$. This situation is illustrated in FIG. 6.

By applying the above analysis with different polarizes-analyzer angles $\alpha_0$. several methods can be developed for (φ, dΔn) determination which will be made clear in the following description.

Generally, for a linear polarized light input impinging into a twisted nematic LC cell, the output polarization is elliptical. However it has been found that there always exists a LC cell orientation such that the output light is also linear polarized. The condition under which a linear polarized input light emerges also linear after passing through a twisted nematic LC cell is referred to as the LP2 condition in the cited reference. It has the following form $$\frac{\phi}{\sqrt{\delta^2+\phi^2}}\tan\sqrt{\delta^2+\phi^2}=\tan 2\alpha^* \quad (6)$$

$$\gamma^*=\phi-\alpha^* \quad (7)$$

where $\delta=\pi d\Delta n/\lambda..\alpha^*$ and $\gamma^*$ are the input and output linear polarized light direction respectively. They are also referred to as the primary and secondary characteristic direction of the LC cell.

If we let the angle between the characteristic directions be $\Psi=\gamma^*-\alpha^*=\phi-2\alpha^*$, then equation (6) can be rewritten as $$\frac{\phi}{\sqrt{\delta^2+\phi^2}}\tan\sqrt{\delta^2+\phi^2}=\tan(\phi-\psi) \quad (8)$$

Equation (8) is important for the characteristic angle methods of ($\phi$, $d\Delta n$)determination.

A detailed description of the preferred embodiments now follows.

FIG. 1 describes the Am preferred embodiment of the new LCD measurement method. The apparatus includes a monochromatic light source 1, a pair of polarizers 2 & 3, a photodetector 4 and the liquid crystal cell under test 5 in between the polarizers 2 & 3. Equation (3) relates the transmission intensity of the light source to the various component orientations and the LC cell parameters ($\phi$, $d\Delta n$). If the polarizer-analyzer angle $\alpha_0 l\sigma\Phi l\xi\epsilon\delta$ and the LC cell is rotated while recording the output light transmission intensity, then $K_1(\Delta_0)$ and $K_2$ can be obtained. By solving equations (4) and (5) simultaneously, ($\phi$, $d\Delta n$) is determined. This is the first measurement method, the fixed angle method. In general it comprises steps 1. With the instrument setup as shown in FIG. 1, fix the polarizes analyzer angle $\alpha_0$.
2. Rotate LC cell while recording photodetector 4 reading.
3. Note the maximum and minimum values of the transmission from step 2.
4. Solve equations (4) and (5) simultaneously to obtain ($\phi$, $d\Delta n$) either graphically or numerically.

Figure 7:
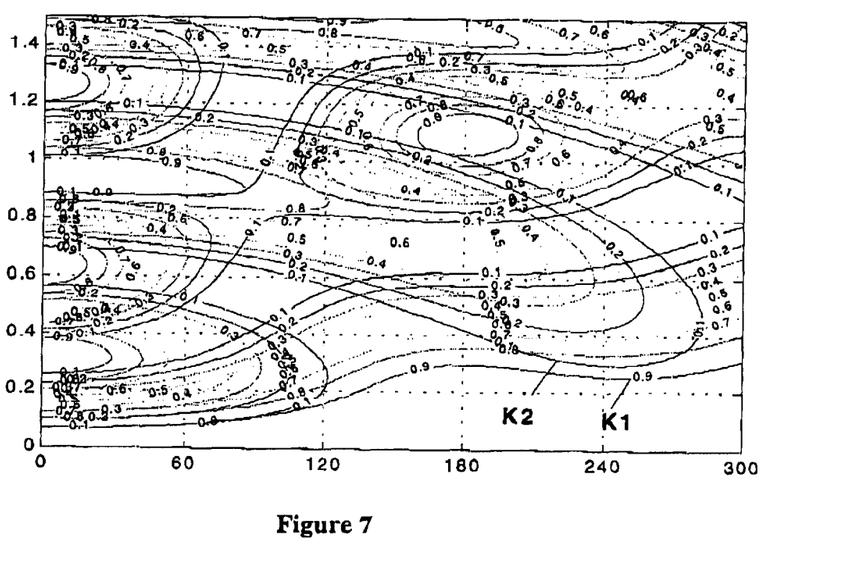
FIG. 7 shows the solution space of equations (4) and (5) with parallel polarizes.
Figure 8:
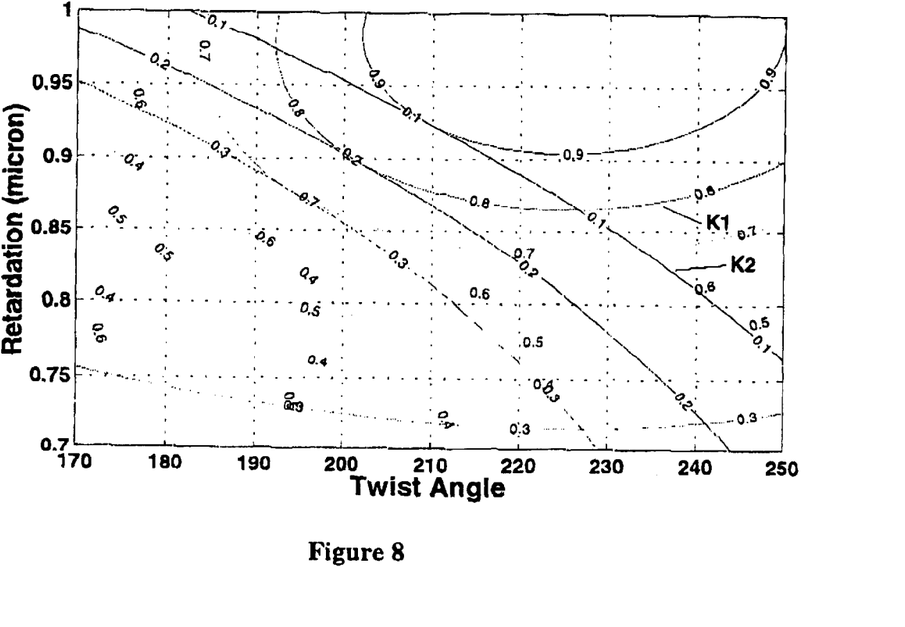
FIG. 8 is the solution space of equations (4) and (5) for STN displays with analyzer angle π/4.
Figure 9:
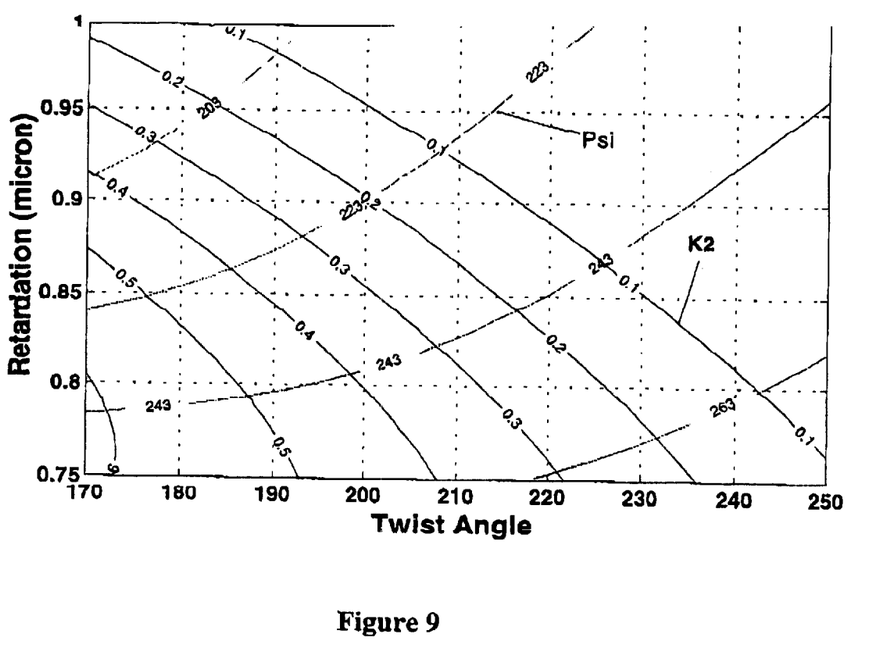
FIG. 9 is the solution space of equations (5) and (8) for STN displays.

A graphical representation of the solution space with parallel polarizers, i.e. $\alpha_0=0$, is shown in FIG. 7. Usually, multiple solutions are found in a large parameter space. However if a proper initial guess is used, a unique solution can be determined. For parallel (or perpendicular) polarizers, the twist sense cannot be determined. However, if $\alpha_0\neq 0$ nor $\pi/2$, then the ambiguity of twist sense can be removed.

In this first preferred embodiment, the polarizer-analyzer angle $\alpha_0$ can be set to zero or $\pi/4$ for ease of data analysis and solving for $\phi$ and $d\Delta n$. However other $\alpha_0$ angles can also be chosen.

In the second preferred embodiment of the present invention, the same optical components and setup as the first preferred embodiment are used. However, the angle between the polarizer and analyzer, $\alpha_0$, is set to a particular value $\Psi$, known as the characteristic angle of the LC cell 5. This may also be termed the characteristic angle method. Polarizer 2 is set to an orientation such that the linear polarized input light remains linear after passing through the LC cell 5. The idea is to obtain the LP2 condition in equation (6). Analyzer 3 is oriented parallel to the output linear polarization. The relation between the LC cell parameters and the characteristic angle $\Psi$ is described by equation (8).

Under this condition, the transmission is unity. If the LC cell is then rotated, the transmission will be described by the following equation:

$$T(\alpha)=1-K_2\sin^2 2(\phi-2\alpha-\Psi) \quad (9)$$

Figure 5:
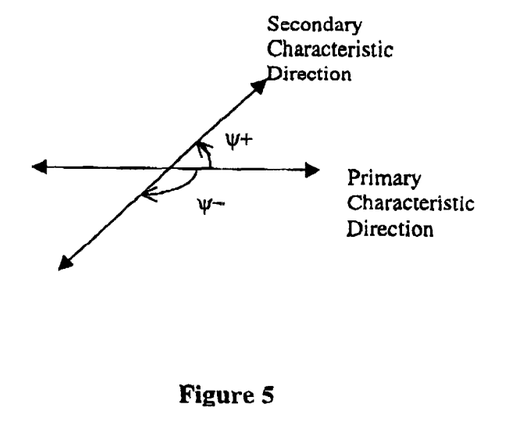
FIG. 5 is an illustration that for every characteristic direction pair, there exists two characteristic angles Ψ+ and Ψ− corresponding to right and left twist.

Again one has a sinusoidally oscillating function. The maximum value of the measured curve equals 1 and the minimum value equals $(1-K_2)$. With known $K_2$ and $\Psi$, one can then solve equations (5) and (8) simultaneously to get ($\phi$, $d\Delta n$). It should be noted that there are always two $\Psi$ values ($\Psi^-$, $\Psi^+$) corresponding to left and right twist of the LC cell as shown in FIG. 5. The procedure for obtaining the LCD parameters using this method therefore consists of 1. With the equipment set-up as shown in FIG. 1 and polarizers in characteristic directions. $\Psi$ is then obtained.
2. Rotate LC cell 5 while recording photodetector 4 reading.
3. Obtain the transmission minimum together with $\Psi$ and then solve equations (5) and (8) simultaneously to obtain ($\phi$, $d\Delta n$).

The method of obtaining the characteristic direction in step 1above comprises steps of:

1. Align the analyzer to be in the same direction as the polarizer.
2. Rotate LC cell 5 to obtain a transmission maximum. Under this condition, the input polarizes bisects the two characteristic directions.
3. With the polarizer 2, the bisector and the analyzer 3 aligned in the same orientation now, rotate LC cell 5 and analyzer 3 with a magnitude ratio of 1:2 until maximum transmission is obtained. Then polarizer 2 and analyzer 3 are in the primacy and secondary characterization directions respectively.

Figure 2:
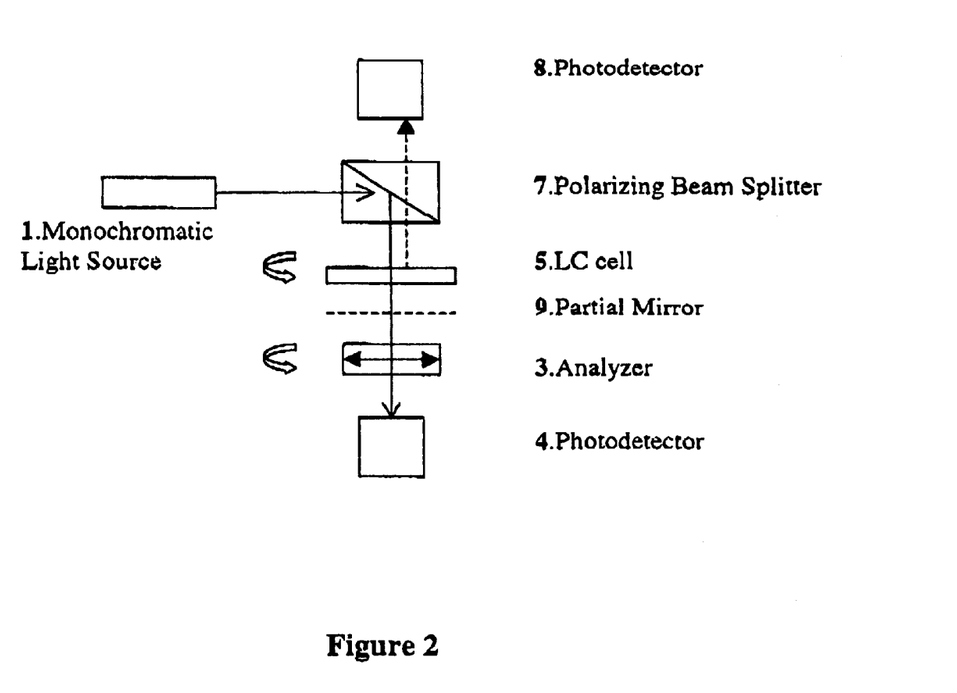
FIG. 2 shows a schematic of a second embodiment of the invention.

FIG. 2 shows the third embodiment of the present invention. This is not a straight path type setup as in FIG. 1, but instead is a T-shaped universal set-up which is applicable to the measurement of both transmissive and reflective LCDs. For transmissive LC cells, this embodiment can carry out the measurement methods as described in the first two embodiments. To realize the fixed angle method measurement, analyzer 3 is set at fixed known angle and LC cell 5 is then rotated to get transmission maximum and minimum in detector 4. To realize the characteristic angle method measurement, the characteristic angle configuration can be set easily by following the procedure described below.

1. First rotate the LC cell until photodetector 8 measures zero intensity. Then the input polarization is in the primary characteristic direction.
2. Fix the LC cell 5 and then rotate the analyzer 3 to get maximum detector 4 reading. Then the analyzer is in the secondary characteristic direction.

For reflective LC cells, in particular twisted nematic LC cells with internal reflectors, the following procedure can determine the retardation.

1. Rotate the reflective LC call 5 until detector 8 obtains zero intensity:
2. Then the retardation value can be obtained by solving equation (6) with known twist angle and rubbing direction in advance.

Figure 3:
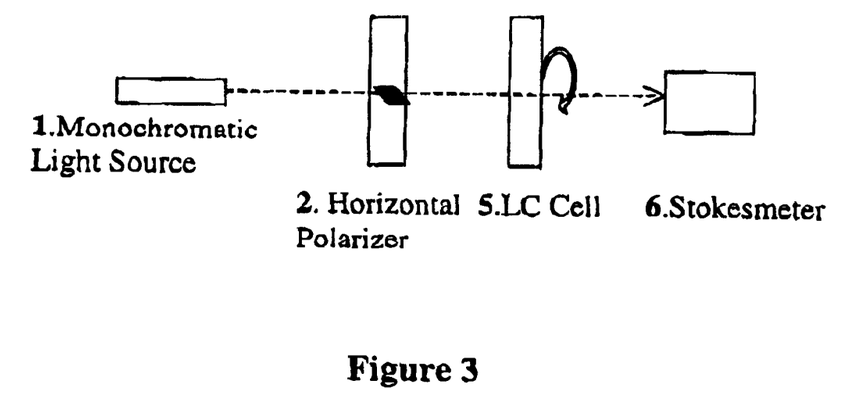
FIG. 3 Shows a schematic of a third embodiment of the invention.

The measuring method described in the fast preferred embodiment needs two intensity measurements to solve for the ($\phi$, $d\Delta n$), and that in the second preferred embodiment needs one intensity measurement and the characteristic angle $\Psi$ to solve for the ($\phi$, $d\Delta n$). The third preferred embodiment uses similar methods as described in the first two preferred embodiments to determine the ($\phi$, $d\Delta n$), but with a T-shaped light path. In order to avoid direct intensity measurement, a new instrument configuration with a Stokesmeter replacing the analyzer 3 and detector 4 as shown in FIG. 3 is disclosed. This can accomplish the above two measurement methods by only taking the Stokes parameters while the LC cell 5 is rotating. This is the fourth preferred embodiment.

Figure 4:
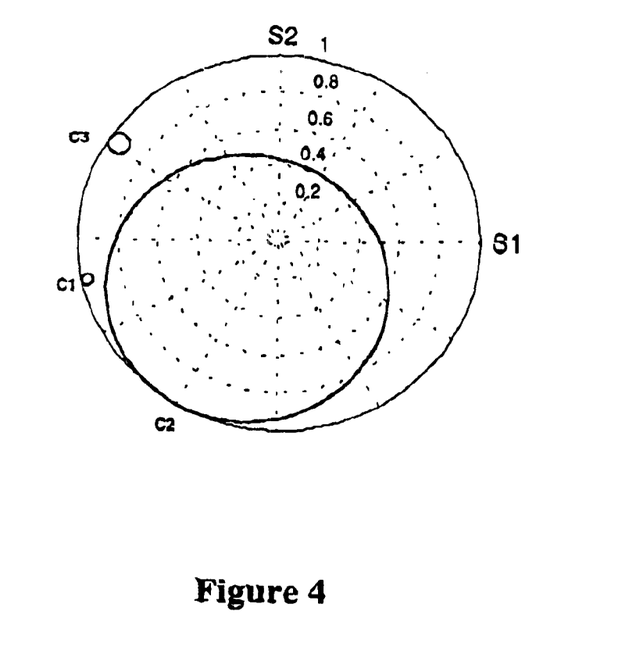
FIG. 4 shows a representative circle of a LC cell drawn as the Poincare sphere.

The following physical fact is helpful to understand these Stokes parameter methods. That is, while any twisted nematic LC cell is rotating, the Stokes vector draws a circle on the Poincare sphere $S_1 S_2$ plane. This is the characteristic circle of the LC cell. Some typical examples are shown in FIG. 4. To simulate the first measurement method with $\alpha_0=0$, only the $S_1$ values of the characteristic circle are necessary. The $S_1$ values correspond to the transmission intensity by the following relation.

$$I_{11} = \frac{1+S_1}{2} \tag{10}$$

To simulate the first measuring method with $\alpha_0=45°$, we have the following equation:

$$I_{45} = \frac{1+S_2}{2} \tag{11}$$

For the simulation of the characteristic angle configuration measuring method, the azimuthal angle of the characteristic circle is equal to the characteristic angle $\Psi$, and then the maximum $|S_3|$ value can replace the minimum intensity required.

By knowing the characteristic angle $\Psi$ and the maximum $|S_3|$ value, one can solve for ($\phi$, d$\Delta$n) by equations (8) and (12).

$$S_3 = \pm J/\cos(\phi - \Psi) \tag{12}$$

where $$J = \frac{-\delta \sin 2\sqrt{\delta^2 + \phi^2}}{\sqrt{\delta^2 + \phi^2}} \tag{13}$$

A general procedure for the Stokes parameter measuring methods is as follows.

1. With the instrument set-up as shown in FIG. 3.
2. Rotate LC cell 5 while recording the Stokes parameters.
3. Get the $S_1$ maximum and minimum and then solve equations (4) and (5) to obtain ($\phi$, d$\Delta$n) through equation (10).
4. Or get the $S_2$ maximum and minimum and then solve equations (5) and (8) to obtain ($\phi$, d$\Delta$n) through equation (11).
5. Or get the characteristic angle $\Psi$ and the maximum $|S_3|$ and then solve equations (8) and (12) simultaneously to obtain ($\phi$, d$\Delta$n).

In addition to the above capabilities, the instrument configuration as shown in FIG. 3 can also be used to evaluate the average tilt angle of a LC cell by the crystal rotation method A procedure described below can be carried out.

1. With the instrument set-up as shown in FIG. 3
2. Rotate the LC cell 5 while recording the Stokes parameters. This time the rotating axis is perpendicular to the light path.
3. Retardation maximum against rotation angle is used to calculate the average tilt angle.

For all the above methods and instrument configurations, it is always possible to use more than one monochromatic light source to double-check the experimental results. Dual wavelength can also be used to eliminate possible ambiguity. This is a fifth preferred embodiment.

In summary, three measurement methods are disclosed, namely the fixed angle method, the characteristic angle method and the Stokes parameter method. Also disclosed are three instrument configurations for LC cell parameter measurement, namely the straight path configuration, the universal T shaped configuration and the Stokesmeter configuration. There are also two methods for obtaining the characteristic directions of a LC cell.

The invention described above may be embodied in other specific forms without departing from the spirit or essential characteristics thereof. The present embodiments are therefore to be considered in all respects as illustrative but not restrictive. The scope of the invention being indicated by the appended claims rather than by the foregoing description and all changes, which come within the meaning and range of equivalency of the claims, are therefore to be embraced therein.

What is claimed is:

1. A method of obtaining the twist angle and retardation value of a liquid crystal cell comprising, locating the liquid crystal cell between a first polarizer and a second polarizer serving as an analyzer, providing an input monochromatic light source and means for measuring the light transmitted through the analyzer, and:

(a) fix the polarizer-analyzer angle $\alpha_0$, at any fixed angle,
(e) rotate the liquid crystal cell while recording the light transmission,
(f) note the maximum ($K_1(\alpha_0)+K_2$) and minimum ($K_1 a \alpha_0$) values of the transmission from step (b), and
(g) solve equations $$K_1(\alpha_0) = \left\{ \cos\beta\cos(\phi - \alpha_0) + \frac{\sin\beta\sin(\phi - \alpha_0)}{\sqrt{1+r^2}} \right\}^2$$

$$K_2 = \frac{r^2}{1+r^2} \sin^2\beta$$

simultaneously to obtain ($\phi$, d$\Delta$n) either graphically or numerically.

2. A method of obtaining the twist angle and retardation value of a liquid crystal cell comprising, locating the liquid crystal cell between a first polarizer and a second polarizes serving as an analyzer, providing an input monochromatic light source and means for measuring the light transmitted through the analyzer, and:

(d) fixing the polarizers in the characteristic directions of said cell whereby the angle ($\Psi$) between said directions is then determined,
(e) rotate the liquid crystal cell while recording the light transmitted through the analyzer,
(f) obtain the transmission minimum (1–$K_2$) and then solve equations $$K_2 = \frac{r^2}{1+r^2} \sin^2\beta$$

$$\frac{\phi}{\sqrt{\delta^2+\phi^2}} \tan\sqrt{\delta^2+\phi^2} = \tan(\phi - \psi)$$

simultaneously to obtain ($\phi$, d$\Delta$n) graphically or numerically.

3. A method of obtaining the twist angle and retardation value of a liquid crystal cell comprising locating said liquid crystal cell between a horizontal polarizer and a Stokesmeter and providing an input source of monochromatic light, and (e) rotating the liquid crystal cell while recording the Stokes parameters, and (f) obtaining the $S_1$ maximum and minimum and then solve equations $$K_1(\alpha_0) = \left\{\cos\beta\cos(\phi - \alpha_0) + \frac{\sin\beta\sin(\phi - \alpha_0)}{\sqrt{1+r^2}}\right\}^2$$

$$K_2 = \frac{r^2}{1+r^2}\sin^2\beta$$

to obtain $(\phi, d\Delta n)$ through the equation $$I_{11} = \frac{1+S_1}{2}, \quad \text{or}$$

(g) obtain the $S_2$ maximum and minimum and then solve equations $$K_2 = \frac{r^2}{1+r^2}\sin^2\beta$$

$$\frac{\phi}{\sqrt{\delta^2 + \phi^2}}\tan\sqrt{\delta^2 + \phi^2} = \tan(\phi - \psi)$$

to obtain $(\phi, d\Delta n)$ through the equation $$I_{45} = \frac{1+S_2}{2}, \quad \text{or}$$

(h) obtain the characteristic angle $\Psi$ and the maximum $|S_3|$ and then solve the equations $$\frac{\phi}{\sqrt{\delta^2 + \phi^2}}\tan\sqrt{\delta^2 + \phi^2} = \tan(\phi - \psi)$$

$$S_3 = \pm J/\cos(\phi - \psi)$$

simultaneously to obtain $(\phi, d\Delta n)$.

4. A method of obtaining the average tilt angle of a liquid crystal cell by a crystal rotation method comprising locating said liquid crystal cell between a horizontal polarizer and a Stokesmeter and providing an input source of monochromatic light, and (d) rotating the liquid crystal cell while recording the Stokes parameters, (e) measure the retardation maximum against rotation angle to calculate the average tilt angle.

5. A method of obtaining the characteristic directions of a liquid crystal cell comprising locating the liquid crystal cell between a first polarizer and a second polarizer serving as an analyzer, providing an input monochromatic light source and means for measuring the light transmitted through the analyzer, and:

(d) aligning the analyzer to be in the same direction as the polarizer, (c) rotating the liquid crystal cell to obtain a transmission maximum wherein the input polarizer bisects the two characteristic directions, (f) with the polarizer, the bisector and the analyzer aligned in the same orientation rotate the liquid crystal cell and analyzer with a magnitude ratio of 1:2 until maximum transmission is obtained wherein the polarizer and analyzer are in the primary and secondary characterization directions respectively.

6. A method of obtaining the characteristic directions of a liquid crystal cell comprising locating the liquid crystal cell between a polarizing beam splitter and a polarizer serving as an analyzer, providing an input monochromatic light source and a first photodetector for measuring the light transmitted through the analyzer and a second photodetector for detecting light reflected from the liquid crystal cell, and:

(a) rotate the liquid crystal cell until the second photodetector measures zero intensity wherein the input polarization is in the primary characteristic direction, (f) fix the liquid crystal cell and then rotate the analyzer to obtain a maximum first photodetector reading wherein the analyzer is in the secondary characteristic direction.

7. A method of obtaining the retardation value of a reflective liquid crystal cell comprising locating the liquid crystal cell between a polarizing beam splitter and a polarizer serving as an analyzer, providing an input monochromatic light source and a first photodetector for measuring the light transmitted through the analyzer and a second photodetector for detecting light reflected from the liquid crystal cell, and:

(c) rotating the reflective liquid crystal cell until the second photodetector measures zero intensity, (d) obtaining the retardation value can be obtained by solving the equation $$\frac{\phi}{\sqrt{\delta^2 + \phi^2}}\tan\sqrt{\delta^2 + \phi^2} = \tan 2\alpha^*$$

with the twist angle and rubbing direction known in advance.

8. Apparatus for measuring the twist angle and retardation value of a liquid crystal cell in accordance with the methods of any of claim 1 comprising a monochromatic light source, an input polarizer, a rotary stage for the a liquid crystal cell under test, a rotary stage for an output analyzer, a photodetector to detect the transmission intensity, and a computer for controlling the rotary stages, receiving data from the photodetector and being programmed to solving the equations:

$$K_1(\alpha_0) = \left\{\cos\beta\cos(\phi - \alpha_0) + \frac{\sin\beta\sin(\phi - \alpha_0)}{\sqrt{1+r^2}}\right\}^2,$$

$$K_2 = \frac{r^2}{1+r^2}\sin^2\beta, \quad \text{and} \quad \frac{\phi}{\sqrt{\delta^2 + \phi^2}}\tan\sqrt{\delta^2 + \phi^2} = \tan(\phi - \psi).$$

9. Apparatus for measuring the twist angle and retardation value and tilt angle of a liquid crystal cell in accordance with the methods of claim 3 comprising a monochromatic light source, an input polarizer, a rotary stage for the liquid crystal cell under test, a Stokesmeter to measure the output light Stokes parameters, and a computer for controlling the rotary stages, receiving data from the Stokesmeter and for solving the equations:

$$K_1(\alpha_0) = \left\{\cos\beta\cos(\phi - \alpha_0) + \frac{\sin\beta\sin(\phi - \alpha_0)}{\sqrt{1+r^2}}\right\}^2,$$

$$K_2 = \frac{r^2}{1+r^2}\sin^2\beta,$$

$$I_{11} = \frac{1+S_1}{2}, \quad \frac{\phi}{\sqrt{\delta^2+\phi^2}}\tan\sqrt{\delta^2+\phi^2} = \tan(\phi = \psi),$$

$$I_{45} = \frac{1+S_2}{2}, \quad \text{and}$$

$$S_3 = \pm J/\cos(\phi-\psi).$$

10. Apparatus for measuring the twist angle and retardation value of a liquid crystal cell in accordance with the methods of any of claim 1 comprising a monochromatic light source, an input polarizing beam splitter, a rotary stage for the liquid crystal cell under test, a partial mirror for characteristic angle setting, a rotary stage for the output analyzer, a first photodetector to detect to transmission intensity, a second photodetector to detect the reflected light intensity, and a computer for controlling the rotary stages, receiving data from the photodetectors and for solving the equations:

$$K_1(\alpha_0) = \left\{\cos\beta\cos(\phi-\alpha_0) + \frac{\sin\beta\sin(\phi-\alpha_0)}{\sqrt{1+r^2}}\right\}^2,$$

$$K_2 = \frac{r^2}{1+r^2}\sin^2\beta, \quad \frac{\phi}{\sqrt{\delta^2+\phi^2}}\tan\sqrt{\delta^2+\phi^2} = \tan 2\alpha^*, \quad \text{and}$$

$$\frac{\phi}{\sqrt{\delta^2+\phi^2}}\tan\sqrt{\delta^2+\phi^2} = \tan(\phi-\psi).$$

11. Apparatus as claimed in any of claims claim 8 comprising two or more monochromatic light sources.

12. Apparatus for measuring the twist angle and retardation value of a liquid crystal cell in accordance with the methods of claim 2, comprising a monochromatic light source, an input polarizer, a rotary stage for the liquid crystal cell under test, a rotary stage for an output analyzer, a photodetector to detect the transmission intensity, and a computer for controlling the rotary stages, receiving data from the photodetector and being programmed to solving the equations:

$$K_1(\alpha_0) = \left\{\cos\beta\cos(\Phi \to \alpha_0) + \frac{\sin\beta\sin(\Phi-\alpha_0)}{\sqrt{1+r^2}}\right\}^2,$$

$$K_2 = \frac{r^2}{1} + r^2\sin^2\beta, \quad \text{and} \quad \frac{\phi}{\sqrt{\delta^2+\phi^2}}\tan\sqrt{\delta^2+\phi^2} = \tan(\phi-\psi).$$

13. Apparatus for measuring the twist angle and retardation value of a liquid crystal cell in accordance with the methods of claim 5, comprising a monochromatic light source, an input polarizer, a rotary stage for the liquid crystal cell under test, a rotary stage for an output analyzer, a photodetector to detect the transmission intensity, and a computer for controlling the rotary stages, receiving data from the photodetector and being programmed to solving the equations:

$$K_1(\alpha_0) = \left\{\cos\beta\cos(\Phi \to \alpha_0) + \frac{\sin\beta\sin(\Phi-\alpha_0)}{\sqrt{1+r^2}}\right\}^2,$$

$$K_2 = \frac{r^2}{1} + r^2\sin^2\beta, \quad \text{and} \quad \frac{\phi}{\sqrt{\delta^2+\phi^2}}\tan\sqrt{\delta^2+\phi^2} = \tan(\phi-\psi).$$

14. Apparatus for measuring the twist angle and retardation value and tilt angle of a liquid crystal cell in accordance with the method of claim 4 comprising a monochromatic light source, an input polarizer, a rotary stage for the liquid crystal cell under test, a Stokesmeter to measure the output light Stokes parameters, and a computer for controlling the rotary stages, receiving data from the Stokesmeter and for solving the equations:

$$K_1(\alpha_0) = \left\{\cos\beta\cos(\phi-\alpha_0) + \frac{\sin\beta\sin(\phi-\alpha_0)}{\sqrt{1+r^2}}\right\}^2,$$

$$K_2 = \frac{r^2}{1+r^2}\sin^2\beta,$$

$$I_{11} = \frac{1+S_1}{2}, \quad \frac{\phi}{\sqrt{\delta^2+\phi^2}}\tan\sqrt{\delta^2+\phi^2} = \tan(\phi = \psi),$$

$$I_{45} = \frac{1+S_2}{2}, \quad \text{and}$$

$$S_3 = \pm J/\cos(\phi-\psi).$$

15. Apparatus for measuring the twist angle and retardation value of a liquid crystal cell in accordance with the methods of claim 2, comprising a monochromatic light source, an input polarizing beam splitter, a rotary stage for the liquid crystal cell under test, a partial mirror for characteristic angle setting, a rotary stage for the output analyzer, a first photodetector to detect the transmission intensity, a second photodetector to detect the reflected light intensity, and a computer for controlling the rotary stages, receiving data from the photodetectors and for solving the equations:

$$K_1(\alpha_0) = \left\{\cos\beta\cos(\Phi \to \alpha_0) + \frac{\sin\beta\sin(\Phi-\alpha_0)}{\sqrt{1+r^2}}\right\}^2,$$

$$K_2 = \frac{r^2}{1} + r^2\sin^2\beta, \quad \text{and} \quad \frac{\phi}{\sqrt{\delta^2+\phi^2}}\tan\sqrt{\delta^2+\phi^2} = \tan(\phi-\psi).$$

16. Apparatus for measuring the twist angle and retardation value of a liquid crystal cell in accordance with the methods of claim 6, comprising a monochromatic light source, an input polarizing beam splitter, a rotary stage for the liquid crystal cell under test, a partial mirror for characteristic angle setting, a rotary stage for the output analyzer, a first photodetector to detect the transmission intensity, a second photodetector to detect the reflected light intensity, and a computer for controlling the rotary stages, receiving data from the photodetectors and for solving the equations:

$$K_1(\alpha_0) = \left\{\cos\beta\cos(\Phi \to \alpha_0) + \frac{\sin\beta\sin(\Phi-\alpha_0)}{\sqrt{1+r^2}}\right\}^2,$$

$$K_2 = \frac{r^2}{1} + r^2\sin^2\beta, \quad \text{and}$$

$$\frac{\phi}{\sqrt{\delta^2+\phi^2}}\tan\sqrt{\delta^2+\phi^2} = \tan 2\alpha^*, \quad \text{and}$$

$$\frac{\phi}{\sqrt{\delta^2+\phi^2}}\tan\sqrt{\delta^2+\phi^2} = \tan(\phi-\psi).$$

17. Apparatus for measuring the twist angle and retardation value of a liquid crystal cell in accordance with the methods of claim 7, comprising a monochromatic light source, an input polarizing beam splitter, a rotary stage for the liquid crystal cell under test, a partial mirror for characteristic angle setting, a rotary stage for the output analyzer, a first photodetector to detect the transmission intensity, a second photodetector to detect the reflected light intensity, and a computer for controlling the rotary stages, receiving data from the photodetectors and for solving the equations:

$$K_1(\alpha_0) = \left\{ \cos\beta\cos(\Phi \to \alpha_0) + \frac{\sin\beta\sin(\Phi - \alpha_0)}{\sqrt{1+r^2}} \right\}^2,$$

$$K_2 = \frac{r^2}{1} + r^2\sin^2\beta, \quad \text{and}$$

$$\frac{\phi}{\sqrt{\delta^2 + \phi^2}} \tan\sqrt{\delta^2 + \phi^2} = \tan 2a^*, \quad \text{and}$$

$$\frac{\phi}{\sqrt{\delta^2 + \phi^2}} \tan\sqrt{\delta^2 + \phi^2} = \tan(\phi - \psi).$$

18. Apparatus as claimed in claim 9, comprising two or more monochromatic light sources.

19. Apparatus as claimed in claim 10, comprising two or more monochromatic light sources.

\* \* \* \* \*